US011523857B2

(12) United States Patent
Godara et al.

(10) Patent No.: US 11,523,857 B2
(45) Date of Patent: Dec. 13, 2022

(54) MULTIPLEXING ALGORITHM WITH POWER ALLOCATION

(71) Applicant: Medtronic, Inc., Minneapolis, MN (US)

(72) Inventors: Neil Godara, Milton (CA); Michael Same, Toronto (CA); Ahmad Khayer Dastjerdi, Toronto (CA)

(73) Assignee: Medtronic, Inc., Minneapolis, MN (US)

( * ) Notice: Subject to any disclaimer, the term of this patent is extended or adjusted under 35 U.S.C. 154(b) by 788 days.

(21) Appl. No.: 16/472,092

(22) PCT Filed: Dec. 21, 2017

(86) PCT No.: PCT/IB2017/058296
§ 371 (c)(1),
(2) Date: Jun. 20, 2019

(87) PCT Pub. No.: WO2018/116247
PCT Pub. Date: Jun. 28, 2018

(65) Prior Publication Data
US 2020/0085487 A1   Mar. 19, 2020

Related U.S. Application Data

(60) Provisional application No. 62/438,336, filed on Dec. 22, 2016.

(51) Int. Cl.
A61B 18/12    (2006.01)
A61B 18/14    (2006.01)
A61B 18/00    (2006.01)

(52) U.S. Cl.
CPC ......... *A61B 18/1206* (2013.01); *A61B 18/14* (2013.01); *A61B 2018/00779* (2013.01); *A61B 2018/00797* (2013.01)

(58) Field of Classification Search
CPC ............... A61B 18/1206; A61B 18/14; A61B 2018/00702; A61B 2018/00779;
(Continued)

(56) References Cited

U.S. PATENT DOCUMENTS 5,300,068 A    4/1994  Rosar et al.
6,346,104 B2 *  2/2002  Daly .......... A61B 18/1206
                                                606/41
(Continued)

FOREIGN PATENT DOCUMENTS

WO   2016014198 A1   1/2016

OTHER PUBLICATIONS

International Search Report and Written Opinion of International Application No. PCT/IB2017/058296, dated Apr. 19, 2018, 8 pp.
(Continued)

*Primary Examiner* — Michael F Peffley
(74) *Attorney, Agent, or Firm* — Shumaker & Sieffert, P.A.

(57) ABSTRACT

A system and method for use with an electrosurgical system for delivering energy to tissue wherein the system includes a generator having a maximum power, at least two channels, and a plurality of probes. The method includes a control system allocating power proportionally to the plurality of probes whereby the probes reach a predetermined threshold without significant delays.

30 Claims, 6 Drawing Sheets

(58) Field of Classification Search
CPC ........... A61B 2018/00791; A61B 2018/00797;
A61B 2018/124; A61B 2018/1273
USPC .......................................................... 606/34
See application file for complete search history.

(56) References Cited

U.S. PATENT DOCUMENTS

| | | | |
|---|---|---|---|
| 6,936,047 B2* | 8/2005 | Nasab | A61B 18/1206 |
| | | | 606/34 |
| 10,980,599 B2* | 4/2021 | McGregor | A61B 18/1206 |
| 2007/0129726 A1 | 6/2007 | Eder et al. | |
| 2010/0324548 A1* | 12/2010 | Godara | A61B 18/1492 |
| | | | 606/34 |
| 2011/0152853 A1 | 6/2011 | Manley et al. | |
| 2017/0049513 A1* | 2/2017 | Cosman, Jr. | A61B 18/1206 |
| 2020/0197070 A1* | 6/2020 | Dastjerdi | A61B 18/14 |

OTHER PUBLICATIONS

International Preliminary Report on Patentability from International Application No. PCT/IB2017/058296, dated Jun. 25, 2019, 4 pp.

* cited by examiner

MULTIPLEXING ALGORITHM WITH POWER ALLOCATION

TECHNICAL FIELD

The disclosure relates to the field of surgical procedures. More specifically, it relates to delivering energy to tissue through energy delivery devices.

SUMMARY

The problem of a number of probes substantially reaching a set temperature (a pre-determined threshold) in the shortest time (i.e. with the shortest delay introduced due to power limitations) when powered by a generator having a maximum power may be solved by a control system allocating power proportionally to the probes such that all of the probes reach the pre-determined threshold at approximately the same time.

In one broad aspect, embodiments of the present invention comprise an electrosurgical system for delivering energy to tissue, the system including; a generator having a maximum output and at least two channels; at least two probes operable to be connected to the at least two channels and to deliver energy; and a control system. The control system, when the at least two probes are connected to the at least two channels, is operable to (a) define a channel requested power for each of the at least two channels, (b) calculate a total requested power using the channel requested power for each of the at least two channels, and (c) determine the power allocated for each of the at least two channels by multiplying the channel requested power of each of the at least two channels with the maximum output and dividing by the total requested power.

In some embodiments, the control system is a component of the generator. In some embodiments, the generator is operable to provide the power allocated for each of the at least two channels.

Some embodiments of the electrosurgical system comprise each of the at least two probes having a temperature sensor for providing a measured temperature to the control system. In some such embodiments, the control system defines the channel requested power for each of the at least two channels based on a temperature error of each of the at least two probes which are attached to the at least two channels, wherein the temperature error of a probe comprises a difference between a set point of the probe and the measured temperature of the probe.

In some embodiments of the first broad aspect, at least one of the at least two probes comprises a monopolar probe. In some embodiments, the at least two probes comprise at least two pairs of bipolar probes, each pair of bipolar probes being operable to be connected to one of the at least two channels.

In some embodiments of the electrosurgical system, the generator comprises four channels. In some embodiments, the maximum output of the generator is from about 1 watt to about 300 watts, while in other embodiments the maximum output is about 50 watts, and in others the maximum output is about 100 watts.

In a second broad aspect, embodiments of the invention comprise a method of delivering energy to at least two electrosurgical devices connected to at least two channels of an electrosurgical generator wherein the electrosurgical generator has a maximum output. The method comprises: defining a channel requested power for each of the at least two channels to which devices are connected; calculating a total requested power using the channel requested power for each of the at least two channels; and determining the power allocated for each of the at least two channels by multiplying the channel requested power of each of the at least two channels with the maximum output and dividing by the total requested power. The method may further comprise the step of a generator providing the power allocated for each of the at least two channels to the at least two electrosurgical devices.

In some embodiments, the electrosurgical generator is operable to receive a temperature measurement from each of the at least two electrosurgical devices connected thereto, the method further comprising monitoring the temperature measurements with a fixed interval of time between readings. In such embodiments, the fixed interval of time is about 10 milliseconds to about 100 milliseconds. In some specific embodiments, the fixed interval of time is about 24 milliseconds.

Some embodiments of the method further comprise, if the total requested power is determined to be less than the maximum output, determining the power allocated for each of the at least two electrosurgical devices to be equal to the channel requested power for that respective electrosurgical device.

In some embodiments of the method, at least one of the at least two electrosurgical devices comprises a monopolar electrosurgical device is connected to a channel. In some embodiments, the at least two electrosurgical devices comprise at least a pair of bipolar electrosurgical devices connected to a channel.

Some embodiments of the second broad aspect further comprise setting each of the at least two electrosurgical devices to an identical set temperature. In some such examples, the identical set temperature is between about 70 degrees Celsius to about 90 degrees Celsius. In some examples, the identical set temperature is about 80 degrees Celsius.

In a third broad aspect, embodiments of the present invention comprise an electrosurgical system for use with at least two probes. The electrosurgical system comprises: a generator having a maximum output and at least two channels which are operable to be connected to the at least two probes, for delivering energy via the at least two probes; and a control system. The control system is operable to, when the at least two probes are connected to the at least two channels, (a) define a channel requested power for each of the at least two channels, (b) calculate a total requested power using the channel requested power for each of the at least two channels, and (c) determine the power allocated for each of the at least two channels by multiplying the channel requested power of each of the at least two channels with the maximum output and dividing by the total requested power. In some embodiments, the control system is a component of the generator.

In some embodiments of this aspect, the generator is operable to provide the power allocated for each of the at least two channels. In some embodiments, the generator defines four channels for delivering energy. In some embodiments, the generator has a maximum output of about 1 watt to about 300 watts. In some specific embodiments the generator has a maximum output of about 50 watts, and in others, of about 100 watts.

In some embodiments of the third broad aspect, the electrosurgical system is operable to read a temperature associated with at least one probe.

BRIEF DESCRIPTION OF THE DRAWINGS

In order that the invention may be readily understood, embodiments of the invention are illustrated by way of examples in the accompanying drawings, in which.

DETAILED DESCRIPTION

Figure 1:
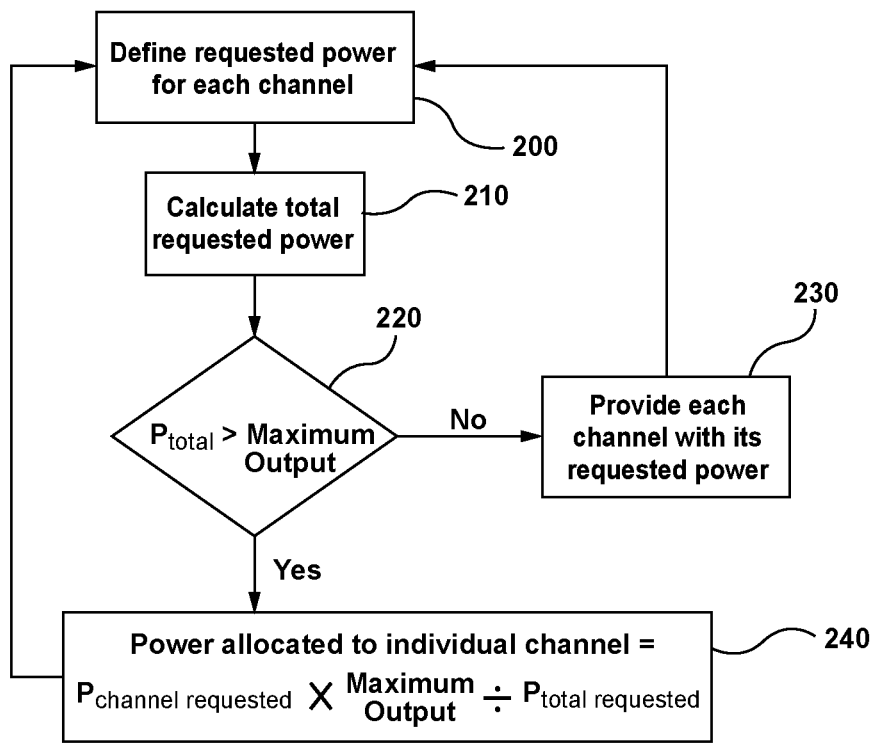
FIG. 1 is an illustration of a flowchart of a control algorithm in accordance with an embodiment of the present invention.

In pain management systems, energy is delivered through probes (i.e. electrosurgical devices) in a temperature controlled manner so as to allow a set temperature to be reached and maintained. Real-time temperature monitoring is achieved through the use of probe sensors e.g. thermocouples at the probe tip. Typically, these systems employ a multiplexing technique involving rapid switching between active channels so as to facilitate effective temperature-controlled energy delivery to multiple channels within a single procedure. A channel is an energy delivery pathway. For various reasons, pain management generators are limited to certain maximum power output levels. For example, for regulatory reasons, many pain management generators have in the past been limited to 50 watts total power output. As a result of a generator having a restricted total output, it can be difficult for sufficient power to be delivered on all active channels so as to facilitate the set temperature being reached in a timely manner (or in the time assigned) and then maintained on all active channels. This is particularly relevant when two or more probes are connected, and/or the probes connected or associated cannulas have relatively large gauges, and/or the probes are located in certain tissue types that require more power to heat. As a result of this limitation, the amount of time that the temperature of each probe remains at a clinically relevant temperature (which is required for effective ablation) can be impacted, thus influencing patient outcomes. In certain cases, algorithms have been developed to automatically add time to the end of the procedure to ensure sufficient ablation time, but these algorithms have limitations, and result in longer overall procedure times. This leads to reduced efficiency and can potentially impact the numbers of patients able to be treated within a given time period.

The present inventors have conceived of and reduced to practice embodiments of systems and methods for all of a number of probes substantially reaching a set temperature (a pre-determined threshold) in the shortest time (i.e. with the shortest delay introduced due to power limitations) when powered by a generator, the systems and methods including a controller of a generator system allocating power proportionally to the probes such that all of the probes reach the pre-determined threshold at approximately the same time. The generator provides the allocated power to channels associated with the probes.

A control system (i.e. a controller) has been developed that varies power delivery between channels. The control system includes an algorithm for determining how to apportion average power effectively between energy delivery channels in an underpowered situation so as to minimize overall procedure time. In particular, the algorithm assists in ensuring that all relevant probes complete ramping and reach and maintain a set temperature with minimal delay due to power restrictions. The types of energy include, at least, electrical energy, electrical power, electrical RF (radiofrequency) energy, and pulsed radiofrequency signals.

The use of the invention will offer benefits to procedure time, and potentially patient outcomes. The invention has particular utility for pain management RF electrical generators. Some embodiments include a bipolar channel comprising two monopolar probes. Some embodiments include a monopolar channel comprising a monopolar probe and a grounding pad. Some embodiments include a combination of monopolar and bipolar channels.

The invention includes an algorithm that uses proportional power allocation when the total power requested by the generator's control strategy to maintain the desired temperature profile across active channels exceeds the maximum capacity of the generator (e.g. nominally 50 watts) i.e. total power required first exceeds the total available power. This algorithm assigns power to the active channels proportionally based on the generator's requested power for each channel. In other words, the delivered power to each channel is calculated by dividing the real-time controller requested power for each channel by the total requested power across all channels at the time and then multiplying by the total power limit (e.g. nominally 50 watts). The controller defines the requested power for each channel based on the temperature error of the channel and the controller parameters assigned by the generator specific to that channel. The requested power for each channel is the power the controller algorithm determines the channel should receive to allow for the minimum heating time. Typically, temperature error is the difference between the control temperature (i.e. the chosen set point) and the measured temperature wherein the temperature is often measured by a sensor in a probe connected to the channel. Certain factors could impact the controller parameters applied to a specific channel including the probe size, probe type and channel configuration (monopolar or bipolar). This algorithm will update in real-time so as to continually scale the delivered power proportionally based on the power requirements of each channel. In some embodiments, updating in real-time comprises monitoring the temperature every 24 ms (milliseconds).

The algorithm is often useful during the ramping phase of energy delivery, during which underpowered situations are common. This algorithm ensures that each channel should ramp up towards the set temperature at similar rates of temperature change, thus all reaching the set temperature at approximately the same time in typical situations. In typical embodiments, each channel has the same (i.e. identical) set temperature. As a result, the situation where one or more channels are delayed to facilitate other channels completing the ramp is substantially minimized. Thus, situations in which different channels are running at the set temperature for substantially different durations are substantially avoided, as is the need to provide additional time for one or more channels. As a result, the total procedure time is minimized.

A feature of the invention is a control strategy that ensures that power is applied proportionately to the channel(s) that require it most, based on the relative requested powers determined by the generator for each channel in real-time. This control strategy could be achieved through various means, including (1) by varying the instantaneous power delivered to each channel, (2) by varying the relative duration (i.e., duty cycle) of power delivery to each channel, or (3) through a hybrid strategy that involves varying both instantaneous power and relative duration in which switching between channels is achieved. All 3 options can apply in underpowered situations. Any of these options can be used as a method of ensuring that the proportional power scaling described herein is applied appropriately.

Each of the 3 options can utilize a control strategy based on discrete time periods. In some embodiments, these time periods are in of the order of 24 ms each and are made up of individual frames of shorter duration (e.g., 2 ms each). The controller determines which channel will deliver energy during each frame, as well as how much instantaneous power will be delivered for the duration of each frame. At the beginning of each time period, the controller can assign the power output for each frame within the longer time periods.

For explanatory purposes, the examples described herein generally use a time period of 24 ms and a frame of 2 ms, this is not intended to be limiting, and alternative embodiments comprise a time period of about 10 ms to about 100 ms and a frame of about 1 ms to about 5 ms.

In option (1) defined above (varying instantaneous power), the number of frames assigned to each channel is fixed throughout, but the instantaneous power within each frame varies based on the controller output. This option can become restrictive in underpowered situations, since channels that need a relatively large proportion of the available power will continue to deliver energy for the same duty cycle. As a result, instantaneous power would have to increase significantly.

In option (2), which includes varying duty cycle, the power output within each frame remains constant but the division of frames between active channels may vary. This option is pertinent in underpowered situations to help continually apply a maximum power (e.g. 50 watts) in times of high power requirements. Notably, this technique typically does not require spikes in instantaneous power, which can be complex to achieve and potentially dangerous. The control strategy manages the requirements of the channel(s) with the most need, while also ensuring that the other channels continue to receive power at sufficient intervals so as not to be adversely affected.

Option (3), which combines options (1) and (2), offers the greatest flexibility. One particular embodiment that utilizes a version of this hybrid method is detailed herein below with respect to FIG. 3C.

When the total power required to deliver energy across all active channels is less than the total available power (e.g. 50 watts), proportional power allocation is not used. In this situation, the duty cycle of each active channel will be identical, the system will multiplex between channels in a set order within each 24 ms time period and each channel will receive all of the power the controller is requesting. If a channel is defined to require more power, the power to that channel is increased based on a power control strategy as long as the total power required across all active channels remains below 50 watts.

In typical embodiments, when total power required first exceeds the total allowable power, or the maximum required instantaneous power is not achievable, the control algorithm uses the proportional power allocation as described herein. For example, in some embodiments, a time period of 24 ms is divided into discrete frames of 2 ms each and the division of frames within a time period by the control algorithm defines the duty cycles of the channels. If needed, the duty cycles can vary from one time period to the next, so as to ensure that the power is proportionally scaled based on requested power. Within each of these discrete frames, the power is delivered to one of the active channels and is typically maintained at close to 50 watts instantaneous power. In this way, the maximum instantaneous power will not typically need to be much above 50 watts.

In some embodiments, instantaneous power can rise slightly above 50 watts (but never above approximately 70 watts) to compensate for some brief down time when switching between channels. In addition, the algorithm also ensures that each active channel receives at least 1 frame within a 24 ms time period. This is to ensure that all channels continue to perform effectively, even those that require very little power. As a result of this, channels that do require more power will be able to receive higher instantaneous power to ensure that the full 50 watts average power is utilized.

Based on the difference between the current temperature of each probe and the control temperature of each probe, as well as each channel's controller parameters, the channel with most need of power will receive the most power. In typical cases, each channel's controller parameters will be identical and power will be apportioned based solely on the relative differences between the current temperature and the control temperature for each probe. The control temperature is the temperature that the probe should ideally be at during any given time period based on a PID (proportional-integral-derivative) control strategy used when the total power required is less than the total available power. This control temperature varies during ramping but matches the set temperature after the ramp time has completed.

The algorithm determines in real time which channel requires the most power and allocates proportionally higher power to that channel.

The algorithm continues to track total power required. When this drops below 50 watts, the control system switches back to regular power control, with the allotment of power determined by actual need without the proportional power allocation described herein i.e. non-proportional power allocation.

The invention is applicable to different types of probes, including internally cooled probes. The invention is pertinent to multi-channel internally cooled RF electrical procedures since the power requirements of internally cooled probes are typically higher than those of their non-cooled counterparts.

Other possible means to help compensate for power supply limitations include staggering the start times of channels, increasing the power limit, or reducing the number of allowable channels.

With specific reference now to the drawings in detail, it is stressed that the particulars shown are by way of example and for purposes of illustrative discussion of certain embodiments of the present invention only. Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Figure 4:
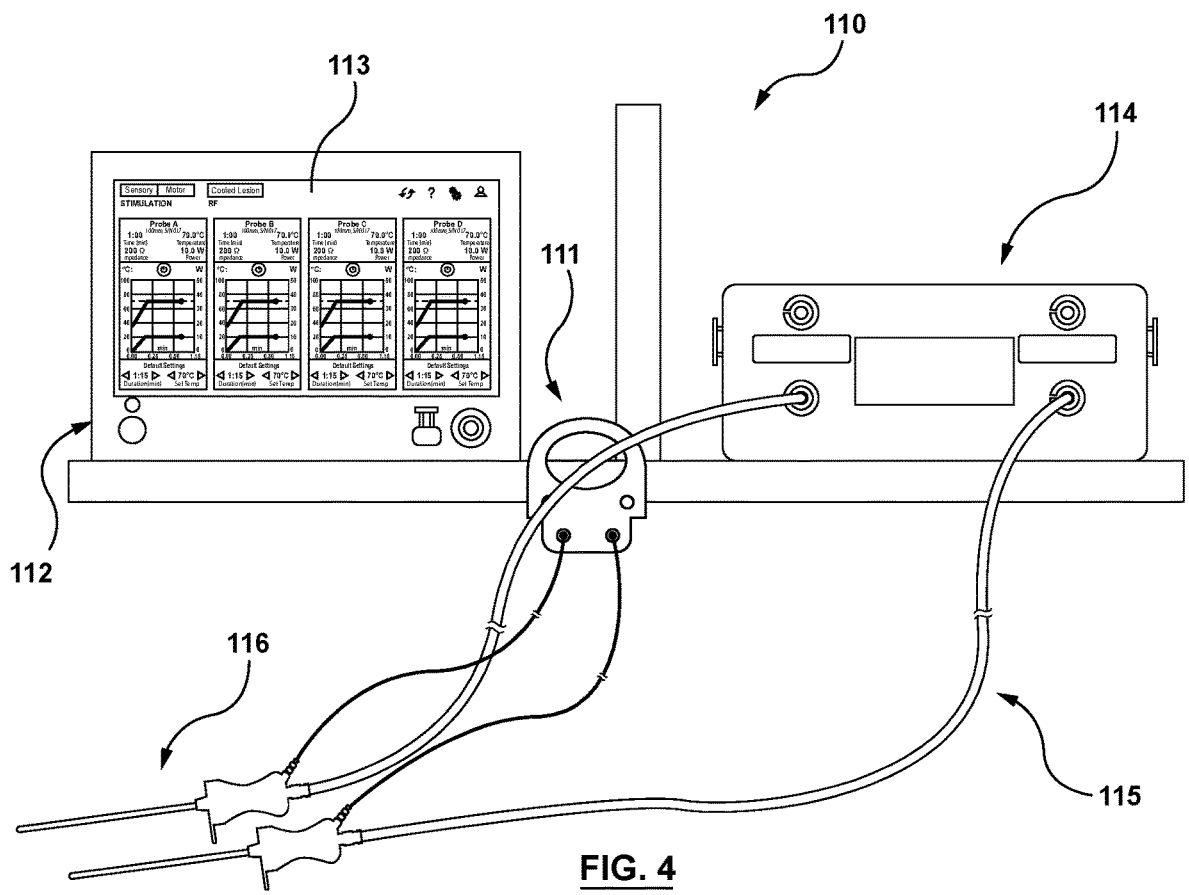
FIG. 4 illustrates an embodiment of a system in accordance with the present invention.

FIG. 4 illustrates an example of a system 110 the algorithm may be used with. System 110 includes a generator 112 having four channels as indicated by GUI 113. For clarity of illustration, FIG. 4 illustrates two probes 116 (rather than three or four probes) which are connected to the channels of generator 112 via way of hub 111, enabling the probes 116 to deliver energy. Hub 111 is connected to the generator 112 via a single cable (not shown in FIG. 4) i.e. there is no cable directly connecting a probe to a channel connector. The hub 111 comprises a plurality of connectors (four) each defining a respective channel. Alternative hub embodiments have less than or more than four connectors. In some alternative embodiments, the probes 116 are connected directly to generator 112 via a plurality of physical connectors on the generator i.e. without the use of a hub such as hub 111. The system of FIG. 4 includes a pump 114 and tubing 115 for providing cooling fluid to probes 116. Some alternative systems only include uncooled probes and accordingly do not include a pump or fluid tubing. The algorithm is applicable to systems comprising cooled probes, uncooled probes, or a combination of cooled and uncooled probes.

FIG. 1 provides a flowchart summarizing the algorithm. In step 200, the controller defines the requested power for each channel based on the temperature error of the channel and the controller parameters for that channel. Typically, temperature error is the difference between the control temperature (i.e. the chosen set point) and the measured temperature with the temperature being measured by a temperature sensor. In step 210, the controller calculates the total requested power, which is the sum of the channel requested power for each of the channels. In step 220, the $P_{total}$ total power requested for all active channels is compared to the Maximum Output of the generator. If the Maximum Output of the generator is greater than the total power requested, then each channel is provided (in step 230) with the requested power as calculated by the controller. From step 230, the algorithm loops back to step 200.

If in step 220, the total $P_{total}$ power requested for all active channels is greater than the Maximum Output of the generator, the power allocated for a channel is determined (in step 240) by multiplying the $P_{channel\ requested}$ channel requested channel P requested power of a channel with the Maximum Output of the generator and dividing the product by the total $P_{total}$ total power requested for all active channels. Step 240 is performed for each channel requiring power. From step 240, the algorithm loops back to step 200. Following the allocation of power by the controller algorithm, the generator provides the allocated power to each of the channels.

Figure 2A:
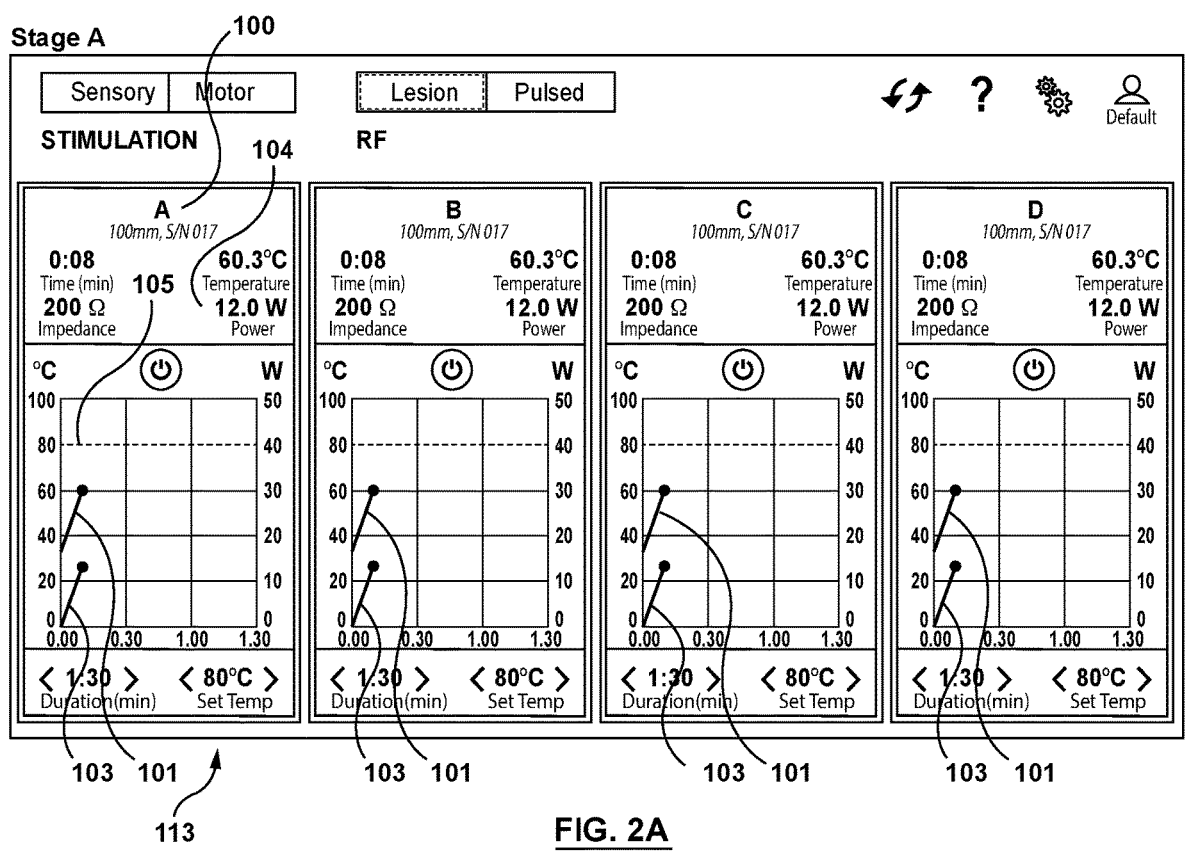
FIGS. 2A to 2C illustrate an algorithm in use in accordance with an embodiment of the present invention.
Figure 2B:
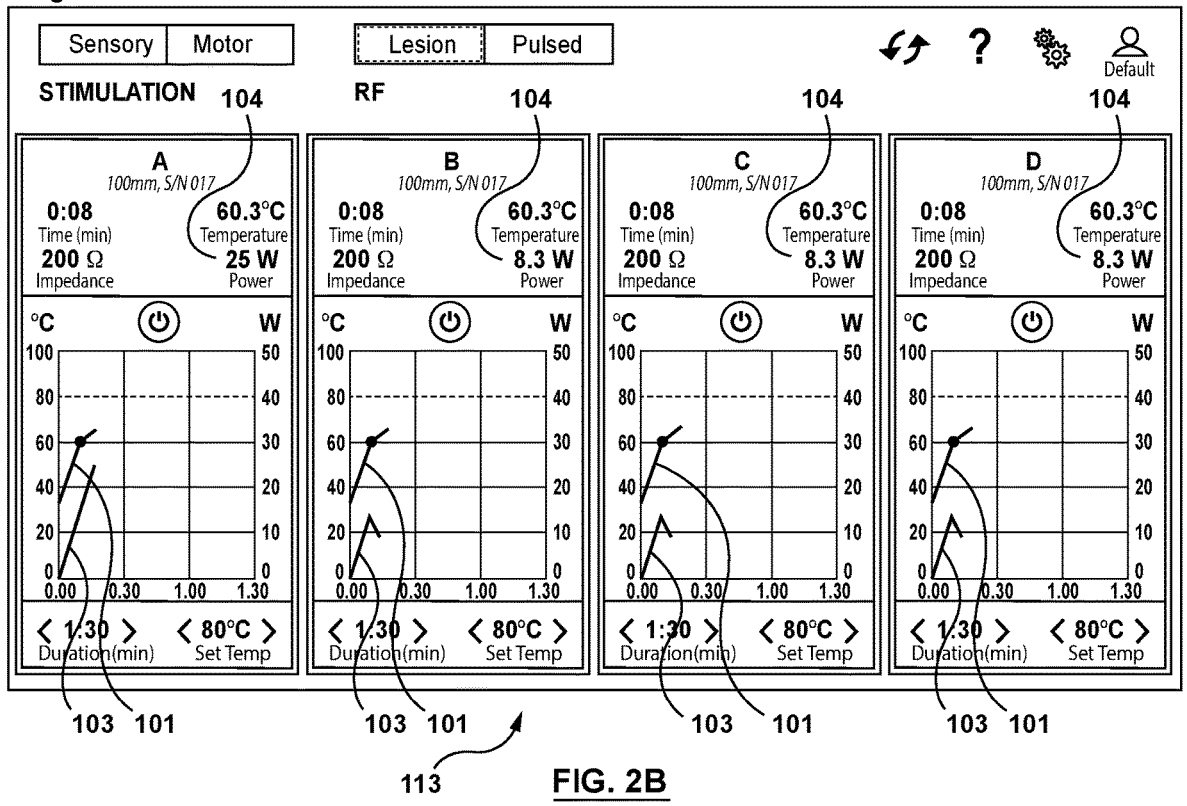
Figure 2C:
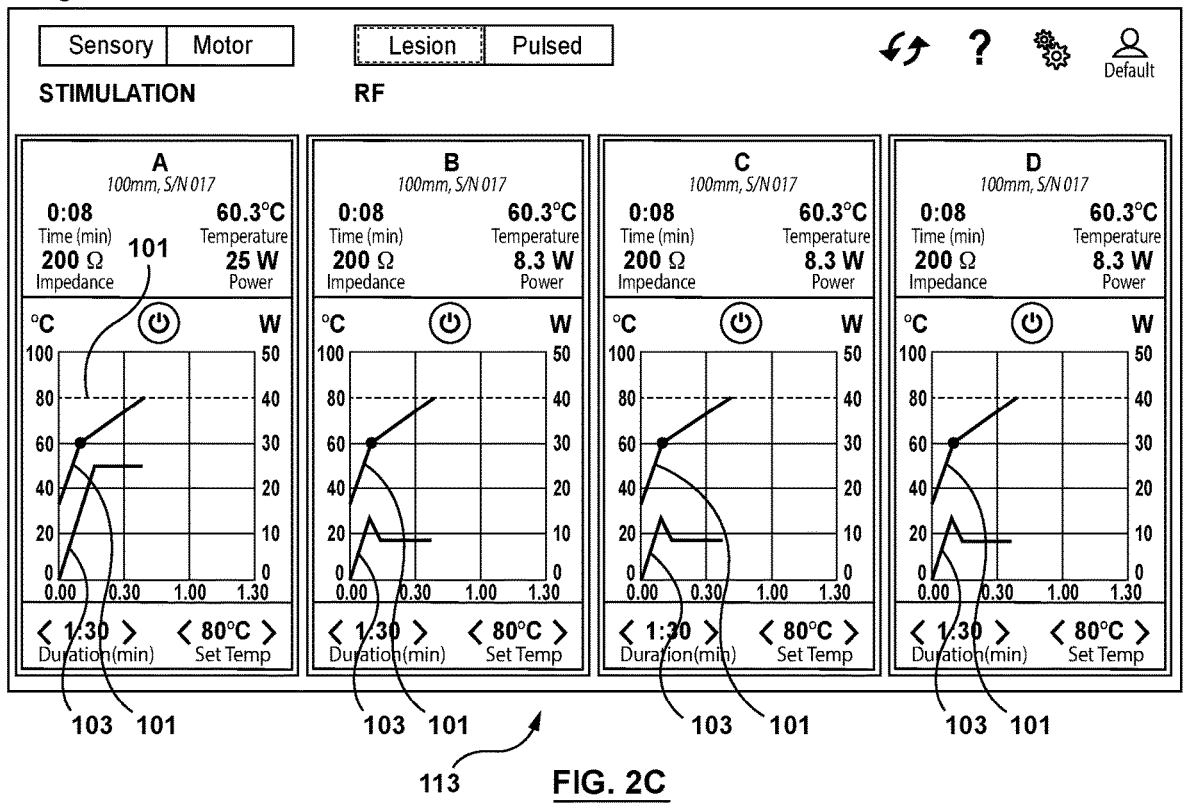

FIGS. 2A to 2C provide graphical examples of power being delivered. In FIG. 2A, four channels are connected and actively delivering RF electrical energy. Channel indicator 100 corresponds with a channel A. The temperature of each channel is ramping at the specified rate. The controller is currently defining a requested power of 12 watts for each channel and 12 watts is being supplied to each channel, as indicated by output power 104. Since the generator system has a 50 watts power limit, there is sufficient power for each channel at this stage. The temperature plots 101 plot the temperatures of the probes attached to the channels. Power plots 103 plot the power levels delivered to the probes.

In FIG. 2B, an underpowered situation has been reached as indicated by the total power across the 4 channels totaling 50 watts (the total shown by the output power 104), resulting in the rate of temperature ramp for each channel decreasing slightly (temperature plot 101). In this example, the controller determines Probe A requires more power than the other probes and therefore more power is delivered to channel A than the other channels. The power requested by the controller for channel A is 30 watts, and the power requested for each of the other channels is 10 watts. As a result, a total of 60 watts is requested which is not feasible since the generator system has a 50 watts power limit. Through the proportional power scaling algorithm described herein, the requested power of each channel will be scaled down by a factor of 50/60 i.e. each of the requested powers is multiplied by 50/60. As a result, Probe A is delivering 25 watts while the other channels (and associated probes) are each delivering 8.3 watts. As a result of this proportional power scaling/allocation, the rate of temperature ramp stays the same across all four channels (temperature plot 101).

In FIG. 2C, the allocated power on each channel is the same as it was in FIG. 2B. As a result of the proportional power scaling, each channel reaches the set temperature 105 at approximately the same time (see temperature plot 101). In a typical RF electrical procedure, the durations at the set temperature 105 for each channel will be the same. As a result, having all channels reach set temperature at the same time will minimize the overall procedure duration.

Some embodiments using standard (un-cooled) probes have a set point of about 80° C., while other embodiments have a set point ranging from about 70° C. to about 90° C. Some embodiments using cooled probes have a set point ranging from about 60° C. to about 75° C.

FIG. 3 provides an example of some different options for the method of controlling power output. The proportional power scaling algorithm could function with any of these methods.

Figure 3A:
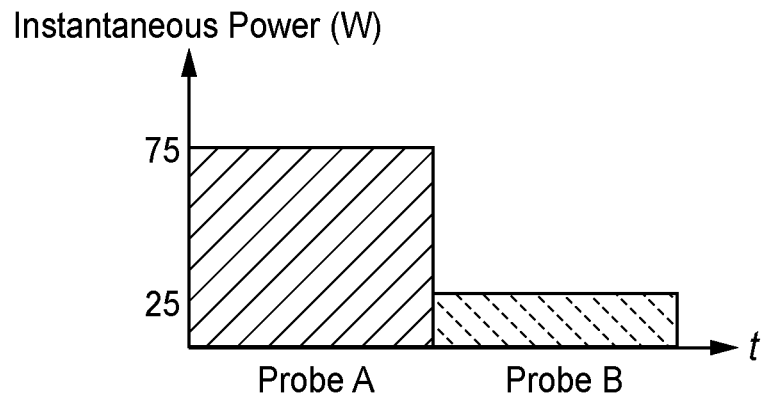
FIGS. 3A to 3C illustrate graphs showing examples of control strategy options.
Figure 3B:
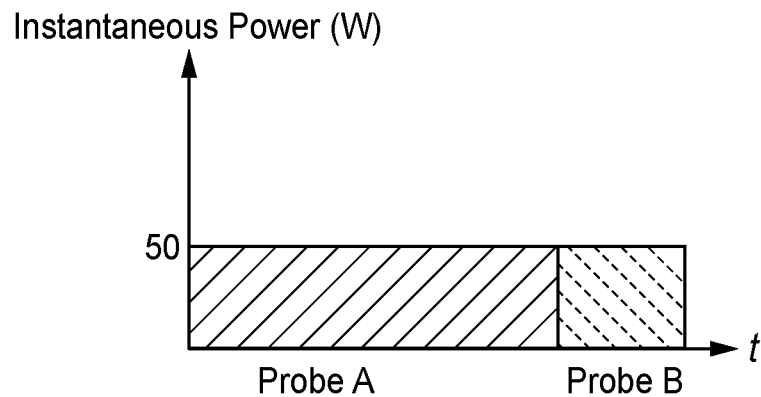
Figure 3C:
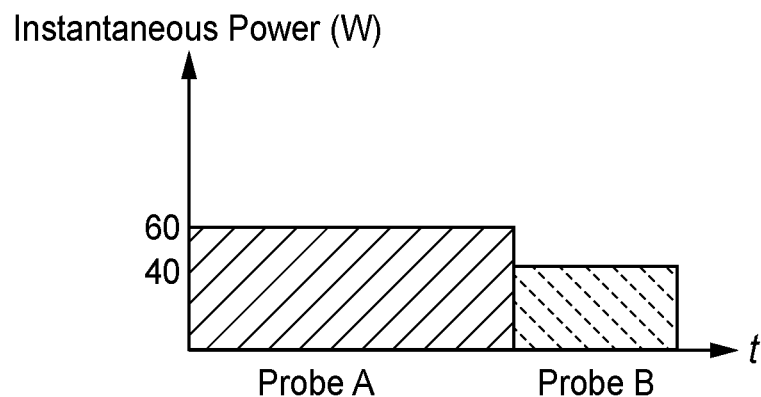

In each of FIGS. 3A, 3B, and 3C, an example is illustrated in which two channels (and the corresponding probes) are active and being allocated a total of 50 watts average power, and Probe A is being allocated three times more power than Probe B.

FIG. 3A depicts a control strategy in which the duty cycle is fixed and the instantaneous power is adjusted to accommodate the average power requirements. In this example, each probe is active for the same duration. Probe A is provided with an instantaneous power of 75 watts.

FIG. 3B depicts a control strategy in which the instantaneous power is fixed and the duty cycle is adjusted. The duty cycle of probe A is three times the duty cycle of probe B. The benefit here is that the instantaneous power doesn't have to increase above 50 watts.

While many pain management generators are limited to 50 watts total power output, other output levels are also possible. Some embodiments of generators have a maximum total output of about 1 watt to about 300 watts. Some specific embodiments have a maximum total output of about 50 watts or about 200 watts. Some examples have a maximum total power output of about 100 watts, with some such examples having a maximum output of 25 watts per channel.

FIG. 3C depicts a hybrid control strategy in which both the instantaneous power and the duty cycle of channel A is increased above that of channel B.

The embodiments of the invention described above are intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment.

Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

We claim:

1. An electrosurgical system for delivering energy to tissue comprising:
   a generator having a maximum output and at least two channels;
   at least two probes operable to be connected to the at least two channels and to deliver energy; and
   a control system, the control system, when the at least two probes are connected to the at least two channels, being operable to (a) define a channel requested power for each of the at least two channels, (b) calculate a total requested power using the channel requested power for each of the at least two channels, and (c) determine a power allocated for each of the at least two channels by multiplying the channel requested power of each of the at least two channels with the maximum output and dividing by the total requested power.

2. The electrosurgical system of claim 1, wherein the control system is a component of the generator.

3. The electrosurgical system of claim 1, wherein the generator is operable to provide the power allocated for each of the at least two channels.

4. The electrosurgical system of claim 1, wherein each of the at least two probes has a temperature sensor for providing a measured temperature to the control system.

5. The electrosurgical system of claim 4, wherein the control system defines the channel requested power for each of the at least two channels based on a temperature error of each of the at least two probes which are attached to the at least two channels, wherein the temperature error of a probe comprises a difference between a set point of the probe and the measured temperature of the probe.

6. The electrosurgical system of claim 1, wherein at least one of the at least two probes comprises a monopolar probe.

7. The electrosurgical system of claim 1, wherein the at least two probes comprise at least two pairs of bipolar probes, each pair of bipolar probes being operable to be connected to one of the at least two channels.

8. The electrosurgical system of claim 1, wherein the generator comprises four channels.

9. The electrosurgical system of claim 1, wherein the maximum output is from about 1 watt to about 300 watts.

10. The electrosurgical system of claim 9, wherein the maximum output is about 50 watts.

11. The electrosurgical system of claim 9, wherein the maximum output is about 100 watts.

12. A method for delivering energy to at least two electrosurgical devices connected to at least two channels of an electrosurgical generator wherein the electrosurgical generator has a maximum output, the method comprising:
    defining a channel requested power for each of the at least two channels to which devices are connected;
    calculating a total requested power using the channel requested power for each of the at least two channels;
    determining a power allocated for each of the at least two channels by multiplying the channel requested power of each of the at least two channels with the maximum output and dividing by the total requested power; and
    controlling the electrosurgical generator to deliver the energy to the at least two electrosurgical devices connected to the at least two channels according to the power allocated for the at least two channels.

13. The method of claim 12, further comprising providing, by the electrosurgical generator, the power allocated for each of the at least two channels to the at least two electrosurgical devices.

14. The method of claim 12, wherein the electrosurgical generator is operable to receive a temperature measurement from each of the at least two electrosurgical devices connected thereto, the method further comprising monitoring the temperature measurements with a fixed interval of time between readings.

15. The method of claim 14, wherein the fixed interval of time is about 10 milliseconds to about 100 milliseconds.

16. The method of claim 15, wherein the fixed interval of time is about 24 milliseconds.

17. The method of claim 12, further comprising:
    if the total requested power is determined to be less than the maximum output, determining the power allocated for each of the at least two electrosurgical devices to be equal to the channel requested power for that respective electrosurgical device.

18. The method of claim 12, wherein at least one of the at least two electrosurgical devices comprises a monopolar electrosurgical device is connected to a channel.

19. The method of claim 12, wherein the at least two electrosurgical devices comprise at least a pair of bipolar electrosurgical devices connected to a channel.

20. The method of claim 12, further comprising setting each of the at least two electrosurgical devices to an identical set temperature.

21. The method of claim 20, wherein the identical set temperature is between about 70 degrees Celsius to about 90 degrees Celsius.

22. The method of claim 21, wherein the identical set temperature is about 80 degrees Celsius.

23. An electrosurgical system for use with at least two probes, the electrosurgical system comprising:
    a generator having a maximum output and at least two channels which are operable to be connected to the at least two probes, for delivering energy via the at least two probes; and
    a control system, being operable to, when the at least two probes are connected to the at least two channels, (a) define a channel requested power for each of the at least two channels, (b) calculate a total requested power using the channel requested power for each of the at least two channels, and (c) determine a power allocated for each of the at least two channels by multiplying the channel requested power of each of the at least two channels with the maximum output and dividing by the total requested power.

24. The electrosurgical system of claim 23, wherein the control system is a component of the generator.

25. The electrosurgical system of claim 23, wherein the generator is operable to provide the power allocated for each of the at least two channels.

26. The electrosurgical system of claim 23, wherein the generator defines four channels for delivering energy.

27. The electrosurgical system of claim 23, wherein the generator has a maximum output of about 1 watt to about 300 watts.

28. The electrosurgical system of claim 27, wherein the generator has a maximum output of about 50 watts.

29. The electrosurgical system of claim 27, wherein the generator has a maximum output of about 100 watts.

30. The electrosurgical system of claim 23, wherein the electrosurgical system is operable to read a temperature associated with at least one probe.

* * * * *